United States Patent
Bielawski et al.

(10) Patent No.: US 6,551,478 B1
(45) Date of Patent: Apr. 22, 2003

(54) FLEXIBLE HIGH-TEMPERATURE PH PROBE

(75) Inventors: John C. Bielawski, Scotia, NY (US); John O. Outwater, Cambridge, MA (US); George P. Halbfinger, Schenectady, NY (US)

(73) Assignee: The United States of America as represented by the Department of Energy, Washington, DC (US)

( * ) Notice: Subject to any disclaimer, the term of this patent is extended or adjusted under 35 U.S.C. 154(b) by 65 days.

(21) Appl. No.: 09/828,209

(22) Filed: Apr. 9, 2001

(51) Int. Cl.$^7$ ............................................. H01M 27/26
(52) U.S. Cl. ...................... 204/433; 204/435
(58) Field of Search ...................... 204/433, 435, 204/419, 416

(56) References Cited

U.S. PATENT DOCUMENTS

| | | | |
|---|---|---|---|
| 4,264,424 A | 4/1981 | Niedrach | |
| 4,329,649 A | 5/1982 | Scoates | |
| 4,406,766 A | 9/1983 | McDonald | |
| 4,500,402 A | * 2/1985 | Miles et al. | 204/435 |
| 4,519,973 A | 5/1985 | Cahalan et al. | |
| 4,575,410 A | 3/1986 | Neti | |
| 5,344,547 A | * 9/1994 | Vlasov et al. | 204/435 |
| 5,407,555 A | * 4/1995 | Winsel | 204/435 |
| 5,516,413 A | * 5/1996 | Foster et al. | 204/435 |
| 5,603,817 A | 2/1997 | Settler et al. | |
| 5,736,029 A | * 4/1998 | Pinkowski | 204/435 |

OTHER PUBLICATIONS

Niedrich; "A New Membrane–Type pH Sensor for Use in High Temperature–High Pressure Water"; J. Electrochem. So. Electrochemical Science and Technology; Oct., 1980; pp. 2122–2130.

* cited by examiner

*Primary Examiner*—Bruce F. Bell
(74) *Attorney, Agent, or Firm*—Julia Cook Moody; Paul A. Gottlieb

(57) ABSTRACT

A flexible pH probe device is provided for use in hot water and other high temperature environments up to about 590° F. The pH probe includes a flexible, inert tubular probe member, an oxygen anion conducting, solid state electrolyte plug located at the distal end of the tubular member, oxide powder disposed at the distal end of the tubular member; a metal wire extending along the tubular member and having a distal end in contact with the oxide powder so as to form therewith an internal reference electrode; and a compression fitting forming a pressure boundary seal around a portion of the tubular member remote from the distal end thereof. Preferably, the tubular member is made of polytetrafluoroethylene, and the solid state electrolyte plug is made of stabilized zirconia. The flexibility of the probe member enables placement of the electrode into the area of interest, including around corners, into confined areas and the like.

8 Claims, 1 Drawing Sheet

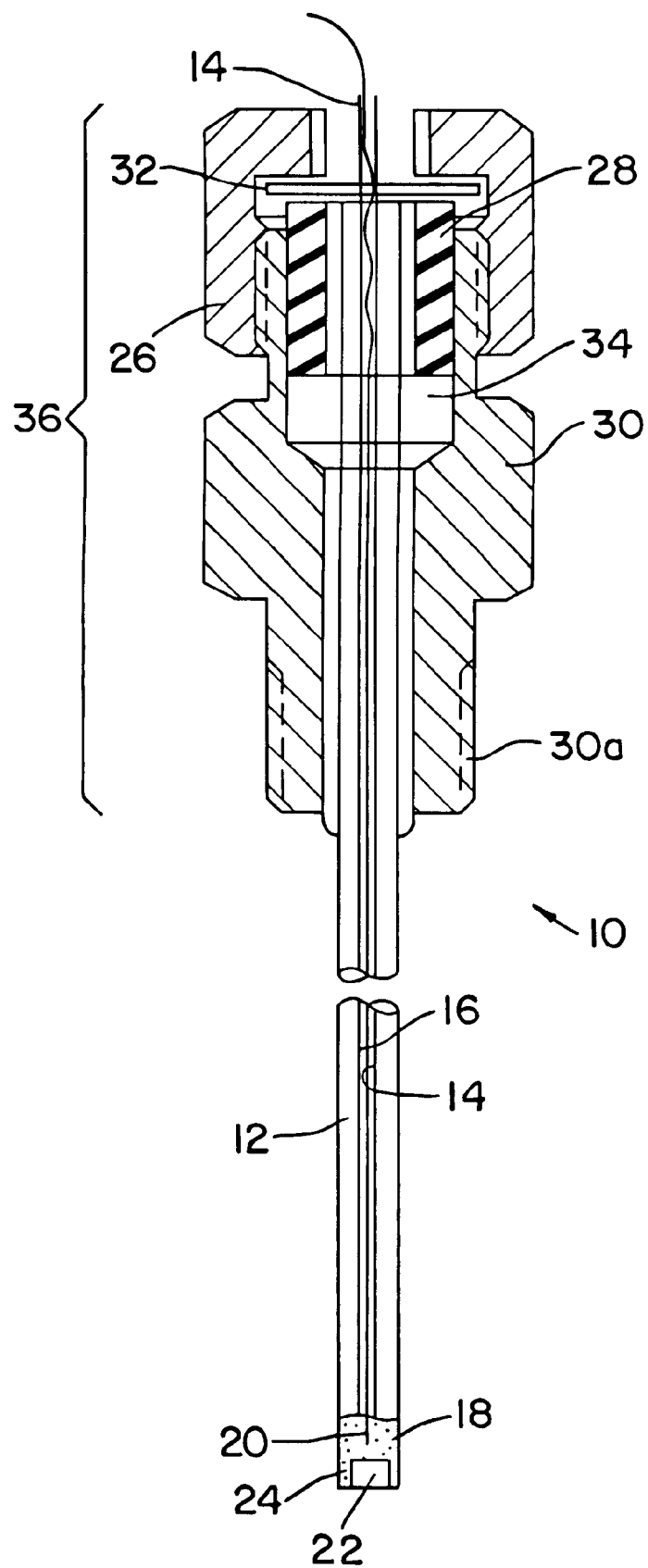

FLEXIBLE HIGH-TEMPERATURE PH PROBE

CONTRACTUAL ORIGIN OF THE INVENTION

The United States Government has rights in this invention under a contract number DE-AC12-76SN00052 with the Department of Energy.

FIELD OF THE INVENTION

This invention generally relates to material tests in hot water and more particularly, to a reference electrode or pH probe for use in material tests in hot water.

BACKGROUND OF THE INVENTION

This invention relates to hydrogen ion, or pH, sensors. Such sensors are employed to determine the content of a specific substance in a fluid or atmosphere. For example, a sensor can be employed to determine the content of oxygen, or carbon dioxide, or the content of hydrogen ions or other ions in solution.

Hydrogen ion sensors are normally utilized for measuring ion concentrations of liquids at approximately ambient temperatures or in some cases, at temperatures ranging up to 150° F. However, innovations such as geothermal wells, nuclear reactors, and the use of other high temperature fluid systems has created a need for a probe that can measure the pH of aqueous fluids at a temperature of 300° F. or higher.

Further, because the pH at certain points in these systems can be of critical importance, there is a need for a pH probe with the flexibility to allow the electrode to be placed within the system precisely where the fluid pH is of most interest. The current state of the art includes the following references: L. W. Niedrach, *Application of Zirconia Membranes as High-Temperature pH Sensors*, General Electric Technical Information Series, No. 83CR0147 (June, 1983); Leonard W. Niedrach, *A New Membrane-Type pH Sensor for Use in High Temperature-High Pressure Water*, J. Electrochemical Soc., Vol. 127 No. 10, p. 2122 (October, 1980); U.S. Pat. No. 4,264,424 to Niedrach; U.S. Pat. No. 4,406,766 to McDonald; and U.S. Pat. No. 4,575,410 to Neti.

The Niedrach-type standard high-temperature pH probe consists, essentially, of a zirconia ceramic tube or sheath surrounding both a metal wire and some form of oxide powder inside of the tube. This tube is supported in a compression fitting, with the fitting forming a pressure boundary seal around the zirconia tube. The potential produced between the internal wire of the electrode and a reference electrode outside of the probe is proportional to the pH of the solution outside the tube. Because the electrode of the Niedrach references uses a gas impervious membrane tube or sheath of an oxygen ion conducting ceramic, and because such ceramics are rigid and brittle, this electrode cannot be bent around corners, or located in restricted regions to measure local pH.

The electrode device of the MacDonald patent is a dual electrode device and includes a chamber to equilibrate pressure (to minimize electrolyte dilution). Ag/AgCl is used as a reference reaction, and the reference reaction is at room temperature. The electrode of the MacDonald patent is not flexible, being a ceramic tube, making the electrode too rigid for some high-temperature applications.

The electrode device of the Neti patent is also a dual electrode device and uses metal/metal halide reference reactions at elevated temperature for the pH sensing electrode. The electrode is usable at high temperatures and pressures, but is not flexible and is too rigid for some applications. A reference electrode is disclosed which can be made of polytetrafluoroethylene, among other materials.

The reliability and accuracy of existing reference electrodes and pH probes at high temperatures is less than optimal. More specifically, existing pH probes are fragile, rigid and difficult to use in various high-temperature applications. In general, prior art pH probes fall into two categories, those which are flexible but cannot perform at temperatures sufficiently high for some applications, and those which sacrifice flexibility and thus are limited in the placement of the probe tip in high-temperature measurements.

In summary, there is currently a need in the art for a pH probe which is flexible enough to enable use thereof in applications that require flexibility, yet which is able to withstand very high temperatures.

SUMMARY OF THE INVENTION

It is, therefore, an object of the invention to provide a pH probe that can function in high-temperature aqueous environments.

It is a further object of the invention to provide a pH probe that is more flexible than conventional high-temperature pH probes.

It is another object of the invention to provide a pH probe that is more durable than conventional high-temperature pH probes.

It is yet another object of the invention to provide a pH probe flexible enough to allow placement of the electrode at virtually any specific point of interest.

As will become apparent, the key advantages of the invention include improved flexibility and reduced fragility, and simplified construction and utilization. The flexibility provided enables placement of the electrode into the area of interest, including around corners, into confined areas and the like. Accordingly, in general, the invention provides a substantially improved pH probe for use in hot water and other relatively high temperature environments, at temperatures above 300° F., and up to about 590° F., and represents a major improvement in the technology.

In accordance with the invention, there is provided a pH probe device comprising: a flexible, inert tubular probe member having a distal end; an oxygen anion conducting, solid state electrolyte plug located at the distal end of the tubular member; oxide powder disposed at the distal end of the tubular member; a metal wire extending along the tubular member and having a distal end in contact with the oxide powder so as to form therewith an internal reference electrode; and a compression fitting forming a pressure boundary seal around a portion of said tubular member remote from the distal end of the tubular member.

Preferably, the tubular member comprises a polytetrafluoroethylene tube.

The oxygen anion conducting, solid state electrolyte plug preferably comprises a zirconia plug and more preferably, a stabilized zirconia plug. Advantageously, the metal of the metal wire and the oxide of the oxide powder of the internal reference electrode are a metal/oxide selected from the group consisting of copper/copper oxide (Cu/CuO), iron/iron oxide ($Fe/Fe_3O_4$), silver/silver oxide ($Ag/Ag_2O$), nickel/nickel oxide (Ni/NiO) and mercury/mercuric oxide (Hg/HgO).

In a preferred implementation, the oxide powder is contained in a chamber located at the distal end of said tubular member and disposed proximally of the plug such that the plug holds said powder within said chamber. Advantageously, the probe further comprises a heat shrink covering holding the plug in place at the distal end of the tubular member. Advantageously, the heat shrink covering comprises polytetrafluoroethylene.

Further features and advantages of the present invention will be set forth in, or apparent from, the detailed description of preferred embodiments thereof which follows.

BRIEF DESCRIPTION OF THE DRAWINGS

The single FIGURE of the drawings is a cross sectional view of a preferred embodiment of the pH probe of the invention.

DETAILED DESCRIPTION OF THE PREFERRED EMBODIMENTS

Referring to the drawings, there is shown a pH probe, generally denoted 10, which is constructed in accordance with a preferred embodiment of the invention and which includes a polytetrafluoroethylene (PTFE) or Teflon® tube 12, the diameter of which is large enough for a connecting wire 14 to pass through. The wire 14, which is typically made of iron or copper, includes a PTFE sheath 16, and extends the length of the PTFE tube 12 to a bored out chamber 18 at the bottom of the tube 12. The chamber 18 holds a substance, indicated at 20, which can react with the metal wire 14 in a thermodynamically predictable manner. For a copper wire, the substance 20 might be a 1:1 mixture of copper and copper oxide powders. For an iron wire, the substance 20 might be a 1:1 mixture of iron and iron oxide powders. For a silver wire, the substance 20 might be a 1:1 mixture of silver and silver oxide. For a nickel wire, the substance 20 might be a 1:1 mixture of nickel and nickel oxide. This substance 20 is retained in chamber 18 by a stabilized zirconia plug 22 (i.e., a plug made of a solid solution of zirconium oxide and another oxide, e.g., calcium or yttrium oxide) which is, in turn, held in place with heat shrink fit PTFE tubing 24.

The top of the PTFE tube 12 is sealed by a compression fitting 36 such as supplied by Conax Corporation of Buffalo, N.Y. A gland follower 28 is located within a central cavity in a probe body member 30 onto which the cap 26 is screwed. The gland follower 28 compresses the gland seal 34 to make a pressure-tight seal. Probe body member 30 includes screw threads 30a at the base thereof which permit screwing of the probe onto an electrode holder (not shown). The gland follower 28 is fabricated of metal and is sized such that the PTFE tubing 12 with the associated wire 14 pass therethrough. The gland seal 34 is fabricated of PTFE and is sized such that the PTFE tube 12 with the associated wire 14 pass therethrough. A metal plate or disk 32 with a hole therein restrains the gland follower 28 so the gland follower 28, along with the PTFE tube 12, cannot extrude out of the top of the cap 26. When the compression fitting 36 is tightened, the PTFE gland seal 34 is compressed, sealing around the PTFE tube 12 which, in turn, seals the wire 14.

The compression fitting 36 can be stood off from the top of the vessel (not shown) on which the probe 10 is mounted so as to keep the gland seal 34 cool.

The metal (e.g., copper) wire 14 disposed at one end in the oxide power (e.g., copper-copper oxide) mixture 20 inside the probe 10 serves as a stable (copper-copper oxide) reference electrode.

The stabilized zirconia plug 22 acts as an electrolyte for the probe 10 and provides for ion transport thereacross. In addition to the reference electrode formed by wire 14 and oxide mixture 20 inside of probe 10, a reference electrode (not shown) is placed outside the probe 10 in a conventional manner. The potential difference between the two electrodes is proportional to the difference in activities of oxygen, which is proportional to the pH in aqueous phase.

The glass wool or quartz wool is in direct contact with the powder oxide and acts to pack the oxide and provide a barrier. The wool is about ½" in the lower part of tube 12.

The flexibility of the PTFE tube 12 permits the probe 10 of the invention to be used at locations in high-temperature applications in a manner which was not previously possible. In this regard, the tip of the probe 10 can be located where the pH is of most interest. In addition, probe 10 is not subject to the breakage that is common with conventional pH probes due to the brittle nature of the zirconia tube used in such probes. The probe of the invention is also, simpler, quicker and less expensive to construct.

In the preferred embodiment described above, there is an upper temperature operating limit of about 590° F.

In a specific, non-limiting example, the metal wire 14 with the heat shrink PTFE tubing 16 is a 30 mil copper wire, restrainer plate 32 is made of steel, fitting 36 is an EGT-250 Conax fitting, PTFE tube 12 is ¼ inch O.D. by 1/16 inch I.D., the heat shrink PTFE tubing 24 is PTFE tubing having an I.D. greater than ¼ inch and plug 22 is of a suitable size to snugly fit in the machined cavity and be held by the heat shrink fit PTFE tubing 24.

Alternate forms of the invention include different internal reference electrodes such as copper/copper oxide, iron/iron oxide, silver/silver oxide, nickel/nickel oxide and mercury/mercuric oxide. Further, other seal materials and configurations can be used. Thus, although the invention has been described above in relation to preferred embodiments thereof, it will be understood by those skilled in the art that variations and modifications can be effected in these preferred embodiments without departing from the scope and spirit of the invention.

What is claimed:

1. A pH probe device comprising: a flexible, inert tubular probe member having a distal end; an oxygen anion conducting, solid state electrolyte plug located at the distal end of said tubular member; oxide powder disposed at the distal end of said tubular member; a metal wire extending along said tubular member and having a distal end in contact with said oxide powder so as to form therewith an internal reference electrode; and a compression fitting forming a pressure boundary seal around a portion of said tubular member remote from the distal end of said tubular member.

2. A pH probe according to claim 1, wherein said tubular member comprises a polytetrafluoroethylene tube.

3. A pH probe according to claim 1, wherein said oxygen anion conducting, solid state electrolyte plug comprises a zirconia plug.

4. A pH probe according to claim 1, wherein said oxygen anion conducting solid state electrolyte plug comprises a stabilized zirconia plug.

5. A pH probe according to claim 4, wherein the metal of said metal wire and the oxide of said oxide powder of said internal reference electrode are a metal/oxide selected from the group consisting of copper/copper oxide, iron/iron oxide, silver/silver oxide, nickel/nickel oxide and mercury/mercuric oxide.

6. A pH probe according to claim 1, wherein said oxide powder is contained in a chamber located at the distal end of said tubular member and disposed proximally of said plug such that said plug holds said powder within said chamber.

7. A pH probe according to claim 6, further comprising a heat shrink tubing holding said plug in place at the distal end of said tubular member.

8. A pH probe according to claim 7, wherein said heat shrink tubing comprises polytetrafluoroethylene.

* * * * *